United States Patent [19]
Erlich

[11] Patent Number: 5,951,551
[45] Date of Patent: Sep. 14, 1999

[54] ELECTROSURGICAL INSTRUMENT HAVING ALTERNATIVE EXTENDABLE TIPS

[76] Inventor: Mark A. Erlich, 800 Fifth Ave., New York, N.Y. 10021

[21] Appl. No.: 09/048,631

[22] Filed: Mar. 26, 1998

[51] Int. Cl.⁶ .................................................. A61B 17/39
[52] U.S. Cl. ............................................... 606/45; 606/49
[58] Field of Search ................................ 606/41, 45–50; 607/101

[56] References Cited

U.S. PATENT DOCUMENTS

| | | | |
|---|---|---|---|
| 3,799,168 | 3/1974 | Peters | 606/45 |
| 5,190,541 | 3/1993 | Abele et al. | 606/46 |
| 5,370,675 | 12/1994 | Edwards et al. | 607/101 |

*Primary Examiner*—Michael Peffley
*Attorney, Agent, or Firm*—Eliot S. Gerber

[57] ABSTRACT

An electrosurgical scalpel includes a hand-held tubular housing having a cable which extends from the housing to an electrosurgical current generator. At least two, and preferably three, conductive blades are retractable to within the housing. The surgeon, using a finger, may selectively extend one blade at a time, so that the extended blade protrudes through a front (distal) orifice of the housing. The blades are different in size and/or shape from each other and may, by finger operation of a switch mounted on the housing, be used for cutting tissue or, alternatively, for applying coagulation current.

7 Claims, 2 Drawing Sheets

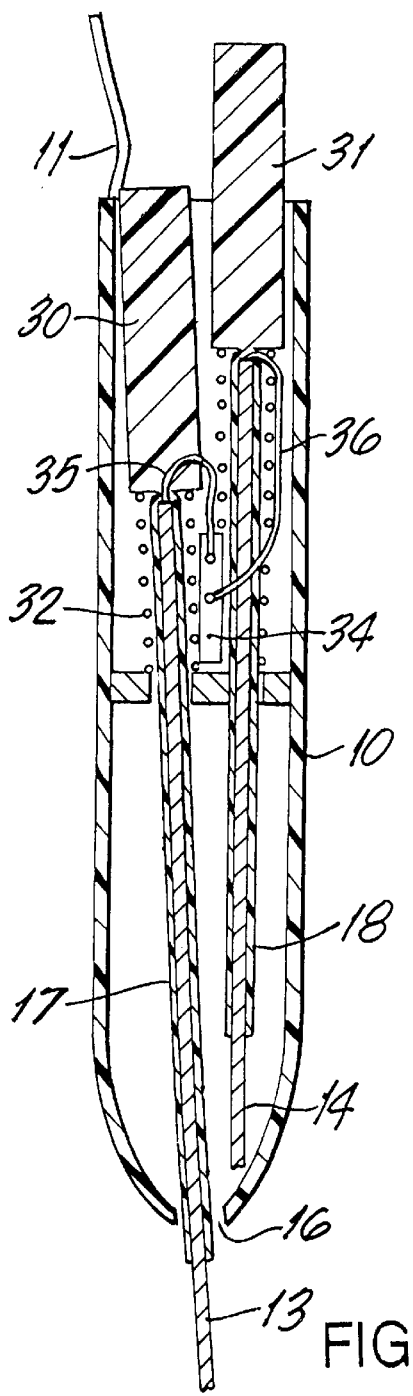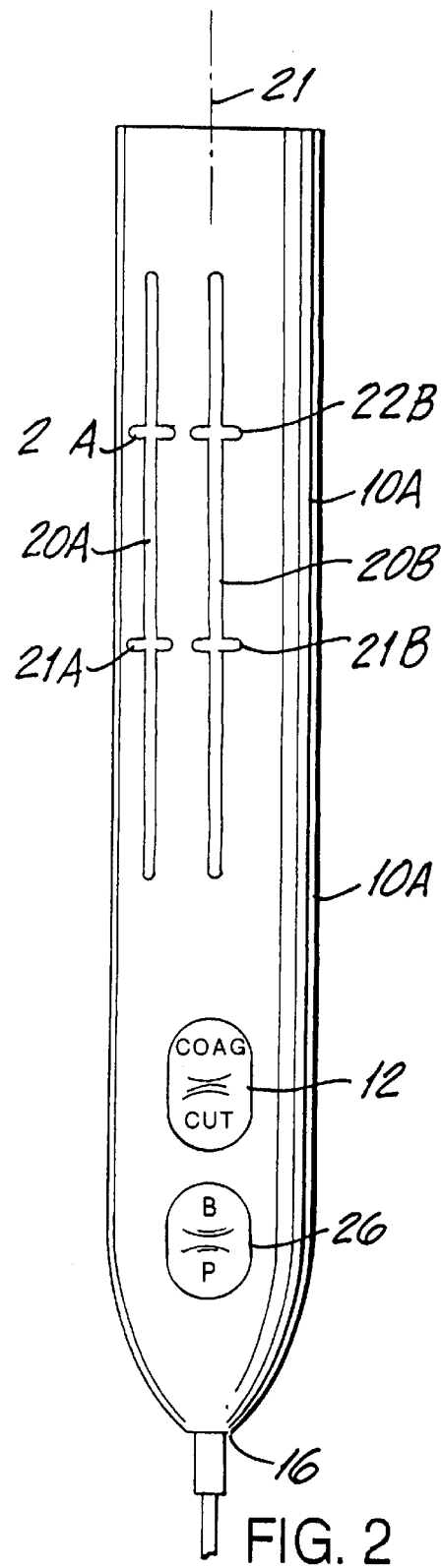

ELECTROSURGICAL INSTRUMENT HAVING ALTERNATIVE EXTENDABLE TIPS

FIELD OF THE INVENTION

The present invention relates to medical devices and more particularly to electrosurgical instruments.

BACKGROUND OF THE INVENTION

At the present time electrosurgical instruments are becoming widely used for all types of surgery. One type of an electrosurgical instrument is a surgical scalpel for cutting the tissue of a patient. Generally such an instrument consists of a body member, which is a non-conductive plastic handle adapted to be held in the surgeon's hand, and a metal conductive blade. When a switch is operated, the blade applies either (i) cutting electrical current so that the blade cuts tissue or (ii) coagulation current so that the blade stops tissue bleeding. The switch may be mounted on the handle and a cable connects the instrument to a regulated current generator, generally using high frequency or radio frequency (RF) alternating current.

Another type of an electrosurgical instrument is used only as an electrocautery device to produce coagulation, without a cutting blade.

In practice, surgeons during an operation do not like to change instruments. They will use an electrosurgical scalpel as an electrocautery device rather than change to a different instrument. However, the electrosurgical scalpel blade is frequently the wrong shape or size to be used as a cautery device. Even if the instruments' generator is switched from the current electrical wave shape and amplitude used for an electrosurgical scalpel to the current more suitable for electrocautery, the blade or top remains the same and may not be ideal for both functions.

In U.S. Pat. No. 5,484,434 to Cartmell et al an electrosurgical scalpel has two finger-operated switches mounted on its handle. The switch selects either an electrosurgical cutting current or, alternatively, an electrosurgical coagulation current, which is transmitted to the conductive blade. The blade is fixed in the handle body.

In U.S. Pat. No. 4,545,375 a handle has two finger-operated switches, one labeled "cut" and the other "coag". The blade is described as a thin knife-like tip which is held in the handle. The entire device is disposable so that it may be used for a single operation.

U.S. Pat. No. 5,290,285 discloses an electrocautery device having a tip with two conductors. In U.S. Pat. No. 4,492,832 the blades are interchangeable and are releasably supported by a central contact element. However, generally surgeons would not want to take the time and bother, during an operation, to change blades by taking one blade out and replacing it with another. If the blades are changed by the surgeon's aid or nurse, the surgeon would have to wait while the blade is being changed, which may interrupt the flow of his movements.

The above-mentioned patents are incorporated by reference herein.

SUMMARY OF THE INVENTION

In accordance with the present invention, an electrosurgical instrument is provided which has at least two, and preferably three or more, differently shaped tips. One tip may be flat and sharp so that it may be used as an electrosurgical scalpel. Another tip may be round (in cross-section) and with a small blunt end so that it may be used for coagulation at a small area. The tips are normally retracted into the handle. One tip at a time may be extended so that it protrudes from the handle by finger movement. Preferably the handle has a conventional switch, such as a rocker type switch, so that the surgeon may select between cutting current and coagulation current. A second rocker switch on the handle may be used to activate (connect) current to an extended tip.

Each of the tips (blades) is connected to a central contact member within the handle, preferably by a low impedance and flexible insulated wire. Since all of the tips are "live", e.g. conductive, the retracted tip (tips) are enclosed in an insulated internal sheath of the handle. Alternatively a switch will apply current automatically to a tip only when it is moved into its extended position.

BRIEF DESCRIPTION OF THE DRAWINGS

The following detailed description of the invention should be considered in connection with the accompanying drawings:

In the drawings:

FIG. 1A is a side cross-sectional view of the first embodiment of the present invention;

FIG. 1B is a top plan view of the embodiment of FIG. 1A;

FIG. 2 is a side plan view of the second embodiment of the present invention;

DETAILED DESCRIPTION OF THE INVENTION

Figure 3:
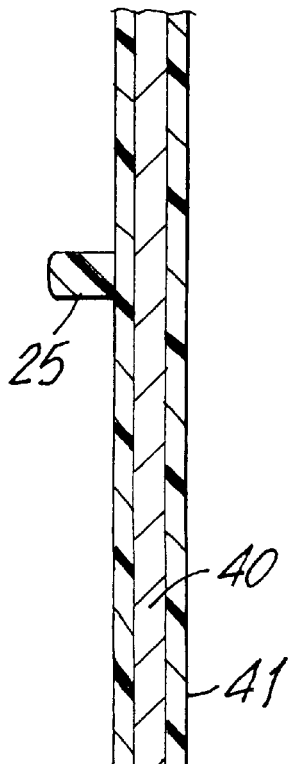
FIG. 3 is an enlarged cross-sectional view of a portion of a tip and its sheath used with the embodiment of FIG. 2.

As shown in FIGS. 1A and 1B, the electrosurgical instrument of the present invention includes a handle 10 (body member) preferably of non-conductive injection-molded plastic and larger than a conventional electrosurgical handle. A cable 11 (electrical wire) leads from the handle 10 to a source of high frequency or RF (Radio Frequency) alternating electrical current. A rocker switch 12 is mounted on handle 10 (not shown in FIG. 1A). Switch 12 is finger-operated and controls an internal switch mechanism which shifts the current from coagulation current to cutting current and vice versa. These portions of the instrument are conventional.

However, the handle 10 also contains two or more, preferably three, tips 13–14. The tips are of different shapes, as shown in FIGS. 4A–5B. Tip 42 is blade-like and tip 43 is round and with a blunt free end. The tips are not fixed in the handle, as in the above-mentioned prior art patents. Instead, each tip is individually slidable forward toward the mouth 16 of the handle and may be extended out through the mouth 16 so that it projects outside of the handle 10. When each tip is so extended it operates like a conventional electrosurgical tip or blade.

As shown in FIGS. 1A and 3, each of the tips 13–14 is mounted in a non-conductive (insulative) round plastic sheath. The tips 13,14 and their sheaths 17,18 are connected to push members 30,31, respectively. The push members 30,31 are hemispherical in cross-section, as shown in FIG 1B. The push members are urged upwards by springs 32,33, respectively. The tips 13,14 are electrically connected to insulative board 34 by flexible insulated wires 35,36 respectively. Connectors on board 34 are connected through rocker switches 12,26 (not shown in the embodiment of FIG. 1A) to cable 11.

In operation, a tip 13 may be extended by finger pressure on push member 30 to extend it out of orifice 16. The tip 13 is held in its extended position (as shown in FIG. 1A) by a latch (not shown).

Figure 4A:
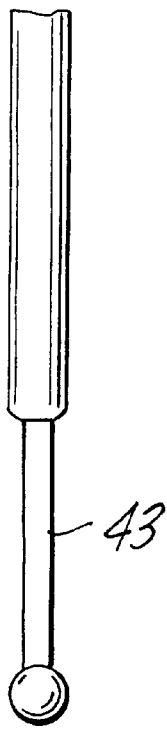
FIGS. 4A and 5A are side plan views of alternative tips which may be used in the embodiments of FIGS. 1A or 2.
Figure 5A:
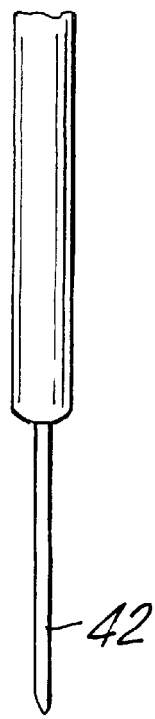
Figure 4B:
FIGS. 4B and 5B are bottom views of the tips of FIGS. 4A and 5A, respectively.
Figure 5B:
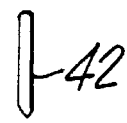

Two alternative tips are shown in FIGS. 4A–5B. The tip of FIGS. 4A–4B is round in cross-section and suitable for spot cauterization. The tip of FIGS. 5A–5B is a flat blade suitable for electrosurgical cutting.

An alternative handle is shown in FIG. 2. It is hollow and has elongated grooves 20A–20B. As shown in FIG. 3 (enlarged) a conductive tip portion 40 is partly enclosed in insulative sheath 41, the tip portion 40 being round in cross-section. An insulative fin 25 having opposite side protrusions 25A extends from sheath 41 and extends outward from axis 21 through a groove 20A or 20B. The surgeon extends, or retracts, a tip by pushing downwards, or upwards, on the fin 25. The fin 25 slides in elongated grooves (channels) 20A,20B in the wall of the handle 10A, the grooves being parallel to the imaginary central axis 21 of the handle 10A. Each of the grooves 20A–20B has two small grooves, respectively 21A–21B and 22A–22B, which are perpendicular to the grooves 20A–20B. These short grooves act as stops for the fins 25 and serve to hold each tip either in its retracted position (within handle 10A) or extended position (protruding from the handle mouth 16A) by capturing the protrusions 25A.

The internal electrical connections depend on the complexity and expense of the circuitry. For example, a switching system may be used to avoid the use of switch 26 and which would use only a single switch 12. In that example, power may automatically be switched only to the extended tip. Alternatively, all of the tips may be "live" (carry current) and the handle insulative.

The illustrated embodiments show two alternative tips. However, more tips, for example, three or four, may be used by using a larger handle. In all cases the tips, at their exposed ends (distal ends) are different in size and/or shape from each other. For example, the different tips include spatula tips ball tips and hemispherical tips (cross section). The tips may be bendable (malleable) by finger pressure. The entire device may be disposable (single use).

I claim:

1. A surgical scalpel for selectively cutting the tissue of a patient using electrosurgical cutting current or alternatively selectively applying coagulation current to said tissue, the currents being generated by an electrosurgical current generator and conducted through a cable to the scalpel, the scalpel comprising:

(a) a tubular housing adapted to be held in a surgeon's hand and having a front orifice;
   (b) manual switch means on said housing to control the current and adapted to be operated by a finger of the surgeon;
   (c) a plurality of at least two electrically conductive scalpel blades;
      (i) the blades being different in size or shape from each other;
      (ii) the blades each being retractable to within the housing and including means for extending the blades, one at a time, through the housing orifice;
      (iii) each blade, when extended, being electrically connectable through the switch means and cable to the current generator so that a blade, when extended, may either cut tissue or apply coagulation current.

2. A scalpel as in claim 1 wherein each blade has a distal and proximate end and an insulative tubular blade holder surrounds the proximate end of each blade.

3. A scalpel as in claim 2 and a finger-operable protrusion on each blade holder adapted to retract or extend the blade holder so that the distal end of the blade is extended out through the orifice or withdrawn within the housing.

4. A scalpel as in claim 1 wherein the plurality is of two blades.

5. A scalpel as in claim 1 wherein at least one blade is especially adapted for electrosurgical cutting and another blade is especially adapted for applying coagulation current.

6. A scalpel as in claim 1 wherein the housing has an imaginary central axis, a housing wall, a plurality of slits in the housing wall which are parallel to the axis, and a protrusion extends through each slit and is connected to a blade and is adapted to be finger-operated to retract the blade into the housing or extend the blade therefrom.

7. A scalpel as in claim 1 and a second switch means mounted on the housing to selectively apply current only to a blade when the handle is extended.

* * * * *